(12) United States Patent
Tachino

(10) Patent No.: US 7,063,980 B2
(45) Date of Patent: Jun. 20, 2006

(54) PRETREATMENT KIT FOR SALIVA AND PRETREATMENT METHOD FOR SALIVA

(75) Inventor: Atsushi Tachino, Tokyo (JP)

(73) Assignee: GC Corporation, Tokyo (JP)

( * ) Notice: Subject to any disclaimer, the term of this patent is extended or adjusted under 35 U.S.C. 154(b) by 237 days.

(21) Appl. No.: 10/645,540

(22) Filed: Aug. 22, 2003

(65) Prior Publication Data

US 2004/0106096 A1    Jun. 3, 2004

(30) Foreign Application Priority Data

Sep. 9, 2002    (JP) ............................. 2002-262838

(51) Int. Cl.
| | |
|---|---|
| *G01N 31/00* | (2006.01) |
| *G01N 1/00* | (2006.01) |
| *G01N 33/531* | (2006.01) |
| *C12P 1/00* | (2006.01) |
| *C12P 7/48* | (2006.01) |

(52) U.S. Cl. .................... 436/17; 252/183.13; 424/9.7; 424/165.1; 424/520; 424/537; 426/531; 426/534; 435/41; 435/144; 436/8; 436/17; 436/174; 436/543; 514/772.1; 524/381

(58) Field of Classification Search ............. 424/78.11, 424/165.1, 537, 9.7, 520; 426/534, 531; 252/183.13; 435/41, 144; 436/174, 8, 17; 514/772.1; 524/381; 562/585

See application file for complete search history.

(56) References Cited

U.S. PATENT DOCUMENTS

| | | | |
|---|---|---|---|
| 4,435,504 A | | 3/1984 | Zuk et al. |
| 5,147,632 A | * | 9/1992 | Pan et al. ...................... 424/54 |
| 5,882,631 A | * | 3/1999 | Suga et al. .................... 424/49 |
| 5,910,420 A | * | 6/1999 | Tuompo et al. ............... 435/18 |
| 6,897,037 B1 | * | 5/2005 | Okada et al. .................. 435/35 |
| 2002/0197738 A1 | * | 12/2002 | Matsumoto et al. | |

FOREIGN PATENT DOCUMENTS

| | | | |
|---|---|---|---|
| EP | 0 660 113 | | 6/1995 |
| EP | 1248106 A1 | * | 3/2002 |
| EP | 1 248 106 | | 10/2002 |
| EP | 1 271 124 | | 1/2003 |
| JP | 2002-35799 | * | 12/2002 |

* cited by examiner

*Primary Examiner*—Lynette R. F. Smith
*Assistant Examiner*—J. Hines
(74) *Attorney, Agent, or Firm*—Oblon, Spivak, McClelland, Maier & Neustadt, P.C.

(57) ABSTRACT

A pretreatment kit and a pretreatment kit for saliva in identification and quantitative determination of mutans streptococci by immunochromatography utilizing an antigen-antibody reaction, which can remove aggregation caused by mucin and chain formation of mutans streptococci in saliva in a simple operation and can efficiently flow out a complex of a labeled antibody and mutans streptococci from a porous membrane retaining the labeled antibody, contains (A) a 0.01 to 10 mol/L aqueous solution of sodium hydroxide, (B) a 0.01 to 3 mol/L aqueous solution of tartaric acid and/or citric acid, and (C) a nonionic surface active agent and/or an amphoteric surface active agent, in which the component (C) is mixed with the components (A) and/or (B), or is provided separately, and at least one substance selected from the particular metallic salts is contained in at least one of the components (A), (B) and (C) in an amount of 5 to 25% by weight.

4 Claims, No Drawings

PRETREATMENT KIT FOR SALIVA AND PRETREATMENT METHOD FOR SALIVA

BACKGROUND OF THE INVENTION

1. Field of the Invention

The present invention relates to a pretreatment kit for saliva for identification and quantitatively determining streptococci mutans, as one of cariogenic bacteria in human saliva, by immunochromatography utilizing an antigen-antibody reaction, and a pretreatment method for saliva using the pretreatment kit for saliva.

2. Description of Conventional Art

It has been known that there is close relation between the presence of streptococci mutans and the generation of dental caries in a human mouth, and therefore, the morbidity risk and the current condition of morbidity can be comprehended to provide benefits to quite a number of people if the presence or absence and the amount of streptococci mutans in a human mouth can be conveniently examined.

An examination technique utilizing an antigen-antibody reaction in examining has been conventionally carried out. For example, the immunoenzymatic technique, which is a method of identification and quantitatively determining with coloring density using an enzyme, requires a special washing device and complicated and accurate operations for handling an antibody and a sample, and also requires an incubator for carrying out an enzyme reaction. The fluorescent antibody technique, which is a method of specifically staining an antigen that is reacted with an antibody labeled with a fluorescent dye, is not commonly employed since a fluorescent microscope is necessary as a measurement device.

Accordingly, various techniques have been proposed for conveniently utilizing an antigen-antibody reaction. Examples thereof include a measurement technique utilizing chromatography (as shown, for example, in U.S. Pat. Nos. 5,591,645, 4,855,240, 4,435,504 and 4,980,298, and Japanese Patent Application Publication Nos. JP-A-61-145459 and JP-A-6-160388). The technique is excellent in simpleness because the presence or absence and the amount of an antigen can be measured only by mixing a body fluid thus collected in a test solution containing an antigen to be identified and quantitatively determined, and then instilling in an examination device. The technique is generally referred to as an immunochromatography technique, and the principles of identification and quantitative determination have been disclosed in detail (as shown, for example, in Se-Hwan Peak, Seung-Hwa Lee, Joung-Hawan Cho and Young-Sang Kim, "Development of rapid One-Step immunochromatographic assay, Methods", vol. 22, p. 53 to 60 (2000)).

It seems that identification and quantitative determination of streptococci mutans in the human mouth can be carried out by applying the technique, but it has not been put into practical use because of the following problems. That is, it is necessary that a sample used for the immunochromatography technique pass through a porous membrane by the capillary phenomenon. However, because the major sample applied to the examination of bacteria in the mouth, such as streptococci mutans, is saliva, a high viscosity substance present in saliva, which is referred to as mucin, clogs the pores of the porous membrane. Furthermore, because mucin has such a function that aggregates epithelial attachment cells stripped off from oral mucosa, the pores of the porous membrane are clogged with these substances to inhibit transmission of streptococci mutans.

In addition to mucin, there is another problem complicating identification and quantitative determination of streptococci mutans by the immunochromatography technique. That is, the streptococci mutans to be measured is a bacterium having a diameter of about 1 μm solely but often forms a chain with 10 to 20 or more bacteria owing to the nature of streptococci, which may be a factor of inhibiting migration in the porous membrane. Furthermore, the streptococci mutans forms glucan having adherence from sucrose in foods and is often severely aggregated. The chain formation and aggregation of streptococci mutans cause clogging in the porous membrane and also reduce the surface area of the streptococci to affect quantitative determination of the number of antigens present on the surface of the streptococci mutans, which reduces accuracy of the measurement.

In the immunochromatography technique, detection of an analytic object is generally carried out by using two antibodies. The first antibody is retained in a porous membrane formed with glass fibers or the like on the side where a sample is dropped, and the antibody is generally labeled with latex particles, gold colloid particles or the like (hereinafter, sometimes referred to as a labeled antibody). In the case where the analytic object to be measured is present in the sample, when passing the sample through the porous membrane, the labeled antibody recognizes the analytic object to be measured and is bonded thereto. The composite of the analytic object and the labeled antibody is flowed by capillary phenomenon toward another porous membrane having the second antibody (hereinafter, sometimes referred to as a trap antibody) immobilized thereon, for example, in the form of strips, and the complex of the analytic object and the labeled antibody is recognized, trapped and detected as a visible signal (in the form of strips in this case). In the case where the immunochromatography technique is applied to saliva as a sample, however, the composite of a labeled antibody and streptococci mutans is trapped in the membrane retaining the labeled antibody but does not efficiently flow by capillary phenomenon toward the porous membrane having the trap antibody immobilized therein to cause such a problem that the accuracy of the measurement is reduced.

SUMMARY OF THE INVENTION

An object of the invention is to solve the problems associated with the conventional technique for identification and quantitative determination of streptococci mutans, as one of cariogenic bacteria in human saliva, by immunochromatography utilizing an antigen-antibody reaction, and to provide a pretreatment kit for saliva and a pretreatment method for saliva in that aggregation caused by mucin and chain formation of streptococci mutans in saliva can be removed in a simple operation, and a complex of a labeled antibody and streptococci mutans effectively flows out from a porous membrane retaining the labeled antibody.

As a result of earnest investigations made by the inventors for solving the problems, it has been found that the following effects can be obtained by treating with particular acid and alkali solutions to complete the present invention.

(1) Mucin and glucan in saliva are dissolved to act on an adventitia of streptococci mutans to suppress aggregation.

(2) Upon using a particular surface active agent in addition thereto, a protein in streptococci mutans is solubilized, whereby the streptococci mutans is efficiently flowed through the porous membrane.

(3) Upon using a particular metallic salt, i.e., sodium chloride, potassium chloride, calcium chloride, magnesium chloride, magnesium sulfate or manganese sulfate, in addition thereto, the complex of a labeled antibody and streptococci mutans can be efficiently flowed out from the membrane retaining the labeled antibody.

The present invention relates to, as one aspect, a pretreatment kit for saliva containing (A) an aqueous solution of sodium hydroxide having a concentration of 0.01 to 10 mol/L, (B) an aqueous solution of tartaric acid and/or citric acid having a concentration of 0.01 to 3 mol/L, and (C) a nonionic surface active agent and/or an amphoteric surface active agent, the component (C) being mixed with at least one of the components (A) and (B), or being provided separately from the components (A) and (B), and at least one substance selected from the group consisting of sodium chloride, potassium chloride, calcium chloride, magnesium chloride, magnesium sulfate and manganese sulfate being contained in at least one of the components (A), (B) and (C) in an amount of 5 to 25% by weight. It is preferred in this aspect that (D) tris(hydroxymethyl)aminomethane is mixed with at least one of the components (A), (B) and (C).

The present invention also relates to, as another aspect, a pretreatment kit for saliva containing (A) an aqueous solution of sodium hydroxide having a concentration of 0.01 to 10 mol/L, (B) an aqueous solution of tartaric acid and/or citric acid having a concentration of 0.01 to 3 mol/L, (C) a nonionic surface active agent and/or an amphoteric surface active agent, and (D) an aqueous solution containing tris(hydroxymethyl) aminomethane, the component (C) being mixed with at least one of the components (A), (B) and (D), or being provided separately from the components (A), (B) and (D), and at least one substance selected from the group consisting of sodium chloride, potassium chloride, calcium chloride, magnesium chloride, magnesium sulfate and manganese sulfate being contained in at least one of the components (A), (B), (C) and (D) in an amount of 5 to 25% by weight.

DESCRIPTION OF THE PREFERRED EMBODIMENTS

It is preferred in the pretreatment kit for saliva of the present invention that the nonionic surface active agent as the component (C) is one kind or a mixture of two or more kinds selected from the group consisting of polyethylene glycol monooctylphenyl ether, n-octyl-β-D-glucoside, n-heptyl-β-D-thioglucoside, n-octyl-β-D-thioglucoside, nonylphenoxy polyethoxyethanol and polyoxyethylene sorbitan monooleate, and the amphoteric surface active agent as the component (C) is one kind or a mixture of two or more kinds selected from the group consisting of CHAPS (3-((3-cholamide-propyl)-dimethylammonio)-1-propanesulfonate) and CHAPSO (3-((3-cholamide-propyl)-dimethylammonio)-1-hydroxypropanesulfonate).

A pretreatment method for saliva in identification and quantitative determination of streptococci mutans by immunochromatography using the pretreatment kit for saliva of the present invention contains, as one aspect, steps of mixing at least one substance selected from the group consisting of sodium chloride, potassium chloride, calcium chloride, magnesium chloride, magnesium sulfate and manganese sulfate with at least one of (A) an aqueous solution of sodium hydroxide having a concentration of 0.01 to 10 mol/L, (B) an aqueous solution of tartaric acid and/or citric acid having a concentration of 0.01 to 3 mol/L, and (C) a nonionic surface active agent and/or an amphoteric surface active agent, in an amount of 5 to 25% by weight; and mixing the components (A), (B) and (C) by dropping in an arbitrary order (hereinafter, referred to as a first method).

The pretreatment method for saliva in identification and quantitative determination of streptococci mutans by immunochromatography also contains, as another aspect, steps of mixing at least one substance selected from the group consisting of sodium chloride, potassium chloride, calcium chloride, magnesium chloride, magnesium sulfate and manganese sulfate with at least one of (A) an aqueous solution of sodium hydroxide having a concentration of 0.01 to 10 mol/L and (B) an aqueous solution of tartaric acid and/or citric acid having a concentration of 0.01 to 3 mol/L, in an amount of 5 to 25% by weight; mixing (C) a nonionic surface active agent and/or an amphoteric surface active agent in at least one of the components (A) and (B); and mixing the components (A) and (B) by dropping in an arbitrary order (hereinafter, referred to as a second method).

The pretreatment method for saliva in identification and quantitative determination of streptococci mutans by immunochromatography also contains, as another aspect, steps of mixing at least one substance selected from the group consisting of sodium chloride, potassium chloride, calcium chloride, magnesium chloride, magnesium sulfate and manganese sulfate with at least one of (A) an aqueous solution of sodium hydroxide having a concentration of 0.01 to 10 mol/L, (B) an aqueous solution of tartaric acid and/or citric acid having a concentration of 0.01 to 3 mol/L, (C) a nonionic surface active agent and/or an amphoteric surface active agent, and (D) tris(hydroxymethyl)aminomethane, in an amount of 5 to 25% by weight; and mixing the components (A), (B), (C) and (D) by dropping in such an order that the component (A) is in contact with the component (B) in the presence of the component (D) (hereinafter, referred to as a third method).

It is preferred in the first method that (D) tris(hydroxymethyl)aminomethane is mixed in at least one of the components (A), (B) and (C), and the components (A), (B) and (C) are mixed by dropping in such an order that the component (A) is in contact with the component (B) in the presence of the component (D) It is preferred in the second method that (D) tris (hydroxymethyl) aminomethane is mixed in at least one of the components (A) and (B), and the components (A) and (B) are mixed by dropping in an arbitrary order. It is preferred in the third method that the component (A), (B) and (D), at least one of which is mixed with the component (C), are mixed by dropping in such an order that the component (A) is in contact with the component (B) in the presence of the component (D).

The aqueous solution of sodium hydroxide having a concentration of 0.01 to 10 mol/L as the component (A) used in the pretreatment kit for saliva and the pretreatment method for saliva according to the present invention exerts a function to act on mucin in saliva and glucan present on an adventitia of streptococci mutans to suppress aggregation of streptococci mutans, so as to facilitate migration of the streptococci mutans as an antigen in the porous membrane. The use of sodium hydroxide as an alkali solution is essential, but sodium carbonate, disodium hydrogen phosphate and the like are not suitable, and the examination of streptococci mutans cannot be carried out with other alkali solutions than sodium hydroxide. It is supposed that this is because an alkali treatment other than sodium hydroxide may impair the structure of the antigen of the streptococci mutans. The concentration of sodium hydroxide in the aqueous solution is necessarily 0.01 to 10 mol/L, and a concentration less than 0.01 mol/L cannot provide sufficient effect, whereas that exceeding 10 mol/L breaks the antigen of the streptococci mutans to deteriorate the detection accuracy.

The aqueous solution of tartaric acid and/or citric acid having a concentration of 0.01 to 3 mol/L as the component (B) used in the pretreatment kit for saliva and the pretreatment method for saliva according to the present invention exerts a function to suppress the chain formation of the streptococci mutans, so as to facilitate migration of the streptococci mutans as an antigen in the porous membrane. The use of tartaric acid and/or citric acid as an acid is essential, but other acids, such as hydrochloric acid, sulfuric acid, nitric acid, acetic acid, lactic acid and maleic acid, are not suitable, and the objective accuracy in examination cannot be obtained even when the other acids are used in combination with sodium hydroxide. It is supposed that this is because the other acids than tartaric acid and citric acid may impair the structure of the antigen of the streptococci mutans. The concentration of tartaric acid and/or citric acid in the aqueous solution is necessarily 0.01 to 3 mol/L, and a concentration less than 0.01 mol/L cannot provide sufficient effect, whereas that exceeding 3 mol/L is not suitable because the solubility of tartaric acid and/or citric acid comes to the limit to form precipitation.

The nonionic surface active agent and/or the amphoteric surface active agent as the component (C) used in the pretreatment kit for saliva and the pretreatment method for saliva according to the present invention exerts a function to solubilize a protein present on the surface of streptococci mutans, so as to facilitate efficient flow of the streptococci mutans through the porous membrane. An ionic surface active agent has been often used in immunochromatography for facilitating smooth migration of a sample solution or an antigen solution within an examination apparatus. However, the surface active agent used in the pretreatment kit for saliva and the pretreatment method for saliva used for identification and quantitative determination of streptococci mutans according to the present invention is necessarily a nonionic surface active agent and/or an amphoteric surface active agent as a result of experimentation, but detection of an antigen with an antibody cannot be attained with an anionic surface active agent, such as sodium lauryl sulfate and sodium dodecylbenzenesulfonate.

The surface active agent used the present invention may be any nonionic surface active agent and/or amphoteric surface active agent without particular limitation, and any of those that are generally used as a solubilizing agent for a membrane protein can be used. The detection sensitivity of streptococci mutans varies depending on the species of the nonionic surface active agent and/or the amphoteric surface active agent used, and it is preferred to use one kind or a mixture of two or more kinds selected from the group consisting of polyethylene glycol monooctylphenyl ether, n-octyl-β-D-glucoside, n-heptyl-β-D-thioglucoside and n-octyl-β-D-thioglucoside as the nonionic surface active agent, and one kind or a mixture of two or more kinds selected from the group consisting of CHAPS (3-((3-cholamide-propyl)-dimethylammonio)-1-propanesulfonate) and CHAPSO (3-((3-cholamide-propyl)-dimethylammonio)-1-hydroxypropanesulfonate) as amphoteric surface active agent, from the standpoint of detection sensitivity.

In the pretreatment kit for saliva and the pretreatment method for saliva according to the present invention, the nonionic surface active agent and/or the amphoteric surface active agent (C) is preferably used to provide a concentration after treatment saliva of 0.05 to 90% by weight. In the case where the concentration is less than 0.05% by weight, it is not preferred since there is such a tendency that the detection sensitivity by the antigen-antibody reaction is lowered, and in the case where it exceeds 90% by weight, it is also not preferred since the detection sensitivity by the antigen-antibody reaction is liable to be lowered.

In the pretreatment kit for saliva and the pretreatment method for saliva according to the present invention, the nonionic surface active agent and/or the amphoteric surface active agent (C) may be provided separately from the aqueous solution of sodium hydroxide having a concentration of 0.01 to 10 mol/L (A) and the aqueous solution of tartaric acid and/or citric acid having a concentration of 0.01 to 3 mol/L (B), and in this case, it may be in the form of an aqueous solution. It may also be provided as a mixture with one or both of the aqueous solution of sodium hydroxide having a concentration of 0.01 to 10 mol/L (A) and the aqueous solution of tartaric acid and/or citric acid having a concentration of 0.01 to 3 mol/L (B), and in this case, attentions are necessarily paid on decomposition property due to acids and alkalis.

In the pretreatment kit for saliva and the pretreatment method for saliva according to the present invention, at least one substance selected from the group consisting of sodium chloride, potassium chloride, calcium chloride, magnesium chloride, magnesium sulfate and manganese sulfate is contained in at least one of the aqueous solution of sodium hydroxide having a concentration of 0.01 to 10 mol/L (A), the aqueous solution of tartaric acid and/or citric acid having a concentration of 0.01 to 3 mol/L (B) and the nonionic surface active agent and/or the amphoteric surface active agent (C), in an amount of 5 to 25% by weight in order to have the complex of the labeled antibody and streptococci mutans flown out from the membrane retaining the labeled antibody efficiently. The at least one substance selected from the group consisting of sodium chloride, potassium chloride, calcium chloride, magnesium chloride, magnesium sulfate and manganese sulfate exerts a function to aggregate various kinds of proteins present in saliva by salting out and counteract the mutual action between the labeled antibody and the membrane retaining the same, so as to provide by the function an effect of facilitating efficient flow of the complex of the labeled antibody and the streptococci mutans from the membrane retaining the labeled antibody.

The at least one substance selected from the group consisting of sodium chloride, potassium chloride, calcium chloride, magnesium chloride, magnesium sulfate and manganese sulfate is necessarily contained in at least one of the aqueous solution of sodium hydroxide having a concentration of 0.01 to 10 mol/L (A), the aqueous solution of tartaric acid and/or citric acid having a concentration of 0.01 to 3 mol/L (B) and the nonionic surface active agent and/or the amphoteric surface active agent (C), in an amount of 5 to 25% by weight. In the case where the amount is less than 5% by weight, the effect cannot be sufficiently obtained, and the complex of the labeled antibody and the streptococci mutans cannot be efficiently flowed out from the membrane retaining the labeled antibody. In the case where it exceeds 25% by weight, on the other hand, the detection accuracy is rather deteriorated.

In the pretreatment kit for saliva and the pretreatment method for saliva according to the present invention, a buffer agent is preferably used since a neutralizing reaction occurs between the aqueous solution of sodium hydroxide having a concentration of 0.01 to 10 mol/L (A) and the aqueous solution of tartaric acid and/or citric acid having a concentration of 0.01 to 3 mol/L (B), and in order to obtain a buffering action efficiently in the neutralizing reaction, tris (hydroxymethyl) aminomethane is preferably used as the buffer agent. At this time, however, it has been confirmed that no sufficient buffering action can be obtained with other buffer agents, such as a combination of sodium hydrogencarbonate and sodium carbonate, and a combination of citric acid and sodium citrate. The tris (hydroxymethyl) aminomethane may be mixed with one of the components (A), (B) and (C), or in alternative, it may be provided separately from them, preferably in the form of an aqueous solution. In the pretreatment kit for saliva according to the present invention, it is necessary that the aqueous solution of sodium hydroxide having a concentration of 0.01 to 10 mol/L (A) and the aqueous solution of tartaric acid and/or citric acid having a concentration of 0.01 to 3 mol/L (B) are provided separately from each other because they cause neutralization.

In the first method according to the present invention, upon identification and quantitative determination of streptococci mutans by immunochromatography, at least one substance selected from the group consisting of sodium chloride, potassium chloride, calcium chloride, magnesium chloride, magnesium sulfate and manganese sulfate is mixed with at least one of the components (A), (B) and (C), in an amount of 5 to 25% by weight, and then the aqueous solution of sodium hydroxide having a concentration of 0.01 to 10 mol/L (A), the aqueous solution of tartaric acid and/or citric acid having a concentration of 0.01 to 3 mol/L (B) and the nonionic surface active agent and/or the amphoteric surface active agent (C) are mixed by dropping in an arbitrary order. In order to simplify the operation in the second method according to the present invention, the nonionic surface active agent and/or the amphoteric surface active agent (C) is mixed with at least one of the aqueous solution of sodium hydroxide having a concentration of 0.01 to 10 mol/L (A) and the aqueous solution of tartaric acid and/or citric acid having a concentration of 0.01 to 3 mol/L (B), and then the aqueous solution of sodium hydroxide having a concentration of 0.01 to 10 mol/L (A) and the aqueous solution of tartaric acid and/or citric acid having a concentration of 0.01 to 3 mol/L (B) are mixed by dropping in an arbitrary order.

In the pretreatment method for saliva according to the present invention, a buffer agent is preferably used since a neutralizing reaction occurs between the aqueous solution of sodium hydroxide having a concentration of 0.01 to 10 mol/L (A) and the aqueous solution of tartaric acid and/or citric acid having a concentration of 0.01 to 3 mol/L (B), and in order to obtain a buffering action efficiently in the neutralizing reaction, tris(hydroxymethyl)aminomethane (D) is preferably used. While the treatments with the components (A), (B) and (C) may be carried out in an arbitrary order since they function independently from each other, it is necessary in the case where the tris(hydroxymethyl)aminomethane (D) is contained in the pretreatment kit for saliva that the components (A) and (B) are in contact with each other in the presence of the tris (hydroxymethyl) aminomethane (D) to obtain a buffering action.

In addition to the first and second methods, in the third method according to the present invention, upon identification and quantitative determination of streptococci mutans by immunochromatography, at least one substance selected from the group consisting of sodium chloride, potassium chloride, calcium chloride, magnesium chloride, magnesium sulfate and manganese sulfate is mixed with at least one of the aqueous solution of sodium hydroxide having a concentration of 0.01 to 10 mol/L (A), the aqueous solution of tartaric acid and/or citric acid having a concentration of 0.01 to 3 mol/L (B), the nonionic surface active agent and/or an amphoteric surface active agent (C), and the tris(hydroxymethyl)aminomethane (D), in an amount of 5 to 25% by weight, and then the components (A), (B), (C) and (D) are mixed by dropping in such an order that the component (A) is in contact with the component (B) in the presence of the component (D). It is preferred in this case that the component (A), (B) and (D), at least one of which is mixed with the component (C), are mixed by dropping in such an order that the component (A) is in contact with the component (B) in the presence of the component (D).

In the pretreatment method for saliva according to the present invention, the treatment is preferably carried out in such a manner that the pH value of saliva after the treatment is in a range of 5 to 9 since the antigen-antibody reaction is carried out within the pH range. While the range varies depending on the antibody used, there is such a tendency that the reliability of the measurement result is lowered when the pH is outside the range since the antibody and the antigen are released from each other, and they exert non-specific affinity.

The sample of saliva having been treated by the pretreatment kit for saliva and the pretreatment method for saliva according to the present invention can be subjected to identification and quantitative determination of streptococci mutans by an antigen-antibody reaction using the conventional immunochromatography technique. The antibody can be obtained by an ordinarily employed way. For example, it may be obtained by the establishment of hybridoma by cell fusion according to Kohler and Milstein (Kohler G, C. Milstein, Continuous cultures of fused cells secreting antibody of predefined specificity, *Nature*, vol. 256, p. 495–497 (1975)), or may be those simply purified from a serum of an animal having been immunized with the antigen.

EXAMPLE

The present invention will be described in detail below with reference to examples, but the present invention is not construed as being limited thereto. Unless otherwise specified, the operations were carried out at room temperature, and the pH values are those at a temperature at 20 to 25° C.

(1) Preparation of Reagent and Test Device

1. Production of Antibodies

Streptococci mutans (ATCC 25175 strain) and Streptococci sobrinus (ATCC 33478 strain) were cultured by using a BHI culture medium (Brain Heart Infusion culture medium, produced by Difco Laboratories) at 37° C. over night, respectively. After collecting bacteria cells from the culture solution by centrifugation, they were washed twice with PBS (10 mmol phosphate buffered saline), and the growth was terminated with a formaldehyde aqueous solution. Mice were directly immunized with the dispersion of the bacteria, and the following two kinds each of purified antibodies were obtained by the establishment of hybridoma using cell fusion by Kohler and Milstein. SM1 antibody: Antibody against Streptococci mutans SM2 antibody: Antibody against Streptococci mutans SS1 antibody: Antibody against Streptococci sobrinus SS2 antibody: Antibody against Streptococci sobrinus 2. Gold Colloid Labeling of Antibody The SM2 antibody and the SS2 antibody were labelled with a gold colloid having a particle diameter of 40 nm. A commercially available gold colloid (produced by British Biocell International) was used, and diluted with PBS having 1% of bovine serum albumin (BSA, a trade name, produced by Sigma-Aldrich Corp.) and 1% of a nonionic surface active agent (Tween 20, a trade name, produced by Sigma-Aldrich Corp.) added thereto to an antibody concentration of 0.1 μg/mL. The antibody solutions labelled with the gold colloid are referred to as SM2 labelled antibody and SS2 labelled antibody, respectively.

3. Production of Antibody-immobilized Porous Film Strip

A nitrocellulose membrane lined with a plastic film (SXHF, a trade name, produced by Millipore Corp. Japan) was used as a porous film. The membrane was cut into a rectangle of 5 mm×40 mm. The SM1 antibody or the SS1 antibody was diluted with a 50 mmol phosphate buffer solution containing 1% of bovine serum albumin to a concentration of 1 mg/mL, and the diluted solution of the antibody was applied on a central part of the nitrocellulose membrane thus cut in the direction perpendicular to the longitudinal direction of the membrane with a micropipet in an amount of about 1 μL/cm. The immobilized antibodies are sometimes referred to as SM1 trap antibody and SS1 trap antibody. Filter paper of 15 mm square as a water absorbing body was fixed on one end of the membrane with a clip to contact closely with each other. A polypropylene matrix (Quick Release Conjugate Pad, a trade name, produced by Millipore Corp. Japan) of 5 mm by 20 mm as a porus membrane retaining the labelled antibody (hereinafter, referred to as a labelled antibody retention) was fixed on the other end of the membrane opposite to the water absorbing body with a clip, on which 30 μL of the SM2 labelled antibody solution or the SS2 labelled antibody solution was dropped. The device was dried at 37° C. for 2 hours and stored in a desiccator until the time of use.

(2) Quantitative Determination of Streptococci Mutans

The results of quantitative determination of streptococci mutans in saliva by the immunochromatography using the foregoing reagents and device was compared with the number of streptococci mutans in saliva by the conventional method of calculation from the number of colonies.

1. Examination Method by Immunochromatography

The reactivity between the streptococci mutans and the antibody immobilized on the antibody-immobilized porous membrane was detected by the following principle. Upon passing saliva through the labelled antibody retention of the antibody-immobilized porous membrane strip, the labelled antibody was bonded to the streptococci mutans in saliva to color in red. The complex of the streptococci mutans and the labelled antibody migrated in the antibody-immobilized porous membrane strip, and it was then trapped by the antibody (trap antibody) immobilized, for example, in the form of strips, in the antibody-immobilized porous membrane strip and thus confirmed as a strip-shape mark.

2. Number of Streptococci mutans by Conventional Calculation from Number of Colonies.

Streptococci mutans, Streptococci sobrinus and foreign bacteria formed colonies on an MSB culture medium. In order that the number of colonies of them were accurately measured, after measuring the number of colonies formed on the MSB culture medium, a part of the colonies was collected and crushed, and the PCR (polymerase chain reaction) is carried out with a synthetic DNA primer having a sequence that is specific in Streptococci mutans or Streptococci sobrinus. The thus amplified gene fragments were subjected to electrophoresis with agarose gel to confirm the strain.

Example 1

Such an antibody-immobilized porous film strip was used that has SM1 antibody immobilized at the central part thereof and SM2 labelled antibody contained in a labelled antibody retention at one end thereof. The examination was carried out in the following manner.

An examination subject was made manducate gum for collecting saliva for 5 minutes to collect saliva in a test tube. A part of the saliva thus collected was diluted with PBS and applied on an MSB culture medium. After anaerobically culturing at 37° C. for 2 or 3 days, the number of colonies was measured. After the measurement, a part of the colonies was collected. After crushing the bacteria cells, a PCR (polymerase chain reaction) was carried out with a synthetic DNA primer having a sequence that is specific in Streptococci mutans or Streptococci sobrinus, and the amplified gene fragments were subjected to electrophoresis with agarose gel to discriminate the strains. The number of bacteria cells (CFU/mL) was calculated from the number of colonies that were confirmed to be those of Streptococci mutans as a result of the discrimination.

A solution (AD solution) was prepared by adding 23.3% by weight of sodium chloride to a solution containing 1.0 mol/L of tris(hydroxymethyl)aminomethane (component (D)) containing 1.0 mol/L of sodium hydroxide (component (A)). A solution (AD solution) was prepared by adding 5% by weight of polyethylene glycol monooctylphenyl ether (produced by Wako Pure Chemical Industries, Ltd.) as a nonionic surface active agent (component (C)) to a solution containing 1.0 mol/L of tris(hydroxymethyl)aminomethane (component (D)) containing 0.5 mol/L of citric acid (component (B)).

50 μL of the AD solution was added to 250 μL of the saliva, followed by stirring, and then 100 μL of the BCD solution was added thereto, followed by stirring. 100 μL out of the saliva thus treated was dropped on the strip on the side of the labelled antibody retention. The solution thus treated had pH of 7.2. The concentration of the component (C) in the solution was 1.25% by weight. After 15 minutes from the dropping, the reaction with the trap antibody was confirmed, and the amount of the complex of the SM2 labelled antibody and Streptococci mutans remaining in the labelled antibody retention was visually observed.

The examination described in the foregoing was carried out for five subjects a to e. The results thus obtained are shown in Table 1 below. The reactivity with the antibody was evaluated for the four grades, i.e., a red strip could be clearly recognized (++), a red strip could be recognized (+), a red strip could be slightly recognized (±), and no strip was recognized (−). The amount of the complex of the SM2 labelled antibody and Streptococci mutans remaining in the labelled antibody retention (hereinafter, simply referred to as a remaining antibody amount) was visually observed and evaluated for the three grades, i.e., a large amount of the remaining antibody could be confirmed as red color in the labelled antibody retention (+), the remaining antibody could be slightly confirmed (±), and none of them was confirmed (−). The unit, CFU/mL, used in the table means the number of colonies of the bacterium per 1 mL of the saliva.

TABLE 1

| Subject | Number of colonies of Streptococci mutans on MSB culture medium (CFU/mL) | Reaction with antibody | Amount of remaining antibody in labelled antibody retention |
|---|---|---|---|
| a | $1.2 \times 10^4$ | − | − |
| b | $2.1 \times 10^5$ | ± | − |
| c | $4.5 \times 10^5$ | + | − |
| d | $7.3 \times 10^5$ | + | ± |
| e | $9.2 \times 10^5$ | ++ | ± |

Example 2

The examination was carried out in the following manner by using an antibody-immobilized porous film strip that was the same as in Example 1 except that SS1 trap antibody was used instead of the SM1 trap antibody, and SS2 labelled antibody was used instead of the SM2 labelled antibody.

A solution (A solution) was prepared by adding 25.0% by weight of sodium chloride to a solution containing 1.0 mol/L of sodium hydroxide (component (A)). A solution (BD solution) was prepared by adding 0.5 mol/L of citric acid (component (B)) to a solution containing 1.0 mol/L of tris(hydroxymethyl) aminomethane (component (D)). An aqueous solution (C solution) containing 5% by weight of polyethylene glycol monooctylphenyl ether (produced by Wako Pure Chemical Industries, Ltd.) as a nonionic surface active agent (component (C)) was prepared.

80 μL of the BD solution was added to 250 μL of the saliva, followed by stirring, 50 μL of the C solution was then added thereto, followed by stirring, and 40 μL of the A solution was finally added thereto, followed by stirring. 100 μL out of the saliva thus treated was dropped on the strip on the side of the labelled antibody retention. The solution thus treated had pH of 6.6. The concentration of the component (C) in the solution was 0.60% by weight. After 15 minutes from the dropping, the reaction with the trap antibody was confirmed, and the amount of the complex of the SS2 labelled antibody and Streptococci sobrinus remaining in the labelled antibody retention was visually observed.

The examination described in the foregoing was carried out for five subjects a to e, and evaluations were carried out in the same manner as in Example 1. The results thus obtained are shown in Table 2 below.

TABLE 2

| Subject | Number of colonies of Streptococci sobrinus on MSB culture medium (CFU/mL) | Reaction with antibody | Amount of remaining antibody in labelled antibody retention |
|---|---|---|---|
| a | $1.4 \times 10^4$ | − | ± |
| b | $4.0 \times 10^5$ | + | − |
| c | $4.4 \times 10^5$ | + | ± |
| d | $9.0 \times 10^5$ | ++ | − |
| e | $9.3 \times 10^5$ | ++ | − |

Example 3

The examination was carried out in the following manner by using an antibody-immobilized porous film strip using the SM1 trap antibody and the SM2 labelled antibody that was the same as in Example 1.

A solution (AC solution) was prepared by adding 1.0 mol/L of sodium hydroxide (component (A)) to an aqueous solution containing 5% by weight of polyethylene glycol monooctylphenyl ether (produced by Wako Pure Chemical Industries, Ltd.) as a nonionic surface active agent (component (C)). A solution (BD solution) was prepared by adding 12.0% by weight of sodium chloride to a solution containing 1.0 mol/L of tris(hydroxymethyl)aminomethane (component (D)) containing 0.5 mol/L of citric acid (component (B)).

75 μL of the AC solution was added to 250 μL of the saliva, followed by stirring, and 75 μL of the BD solution was then added thereto, followed by stirring. 100 μL out of the saliva thus treated was dropped on the strip on the side of the labelled antibody retention. The solution thus treated had pH of 7.5. The concentration of the component (C) in the solution was 0.94% by weight. After 15 minutes from the dropping, the reaction with the trap antibody was confirmed, and the amount of the complex of the SM2 labelled antibody and Streptococci mutans remaining in the labelled antibody retention was visually observed.

The examination described in the foregoing was carried out for three subjects a to c, and evaluations were carried out in the same manner as in Example 1. The results thus obtained are shown in Table 3 below.

TABLE 3

| Subject | Number of colonies of Streptococci mutans on MSB culture medium (CFU/mL) | Reaction with antibody | Amount of remaining antibody in labelled antibody retention |
|---|---|---|---|
| a | $1.2 \times 10^4$ | − | − |
| b | $4.3 \times 10^5$ | + | − |
| c | $8.4 \times 10^5$ | ++ | − |

Example 4

The examination was carried out in the following manner by using an antibody-immobilized porous film strip using the SS1 trap antibody and the SS2 labelled antibody that was the same as in Example 2.

An aqueous solution (A solution) containing 4.0 mol/L of sodium hydroxide (component (A)) was prepared. An aqueous solution (B solution) containing 1.0 mol/L of tartaric acid (component (B)) was prepared. An aqueous solution (C solution) containing 5% by weight of polyethylene glycol monooctylphenyl ether (produced by Wako Pure Chemical Industries, Ltd.) as a nonionic surface active agent (component (C)) was prepared. A solution (D solution) was prepared by adding 12.0% by weight of sodium chloride to a solution containing 1.0 mol/L of tris(hydroxymethyl)aminomethane (component (D)).

40 μL of the C solution was added to 250 μL of the saliva, followed by stirring, 40 μL of the B solution was then added thereto, followed by stirring, 40 μL of the D solution was further added thereto, followed by stirring, and 40 μL of the A solution was finally added thereto, followed by stirring. 100 μL out of the saliva thus treated was dropped on the strip on the side of the labelled antibody retention. The solution thus treated had pH of 8.0. The concentration of the component (C) in the solution was 0.49% by weight. After 15 minutes from the dropping, the reaction with the trap antibody was confirmed, and the amount of the complex of the SS2 labelled antibody and Streptococci sobrinus remaining in the labelled antibody retention was visually observed.

The examination described in the foregoing was carried out for three subjects a to c, and evaluations were carried out in the same manner as in Example 1. The results thus obtained are shown in Table 4 below.

TABLE 4

| Subject | Number of colonies of Streptococci sobrinus on MSB culture medium (CFU/mL) | Reaction with antibody | Amount of remaining antibody in labelled antibody retention |
|---------|---|---|---|
| a | $1.0 \times 10^4$ | − | − |
| b | $3.9 \times 10^5$ | + | ± |
| c | $7.7 \times 10^5$ | ++ | − |

Example 5

The examination was carried out in the following manner by using an antibody-immobilized porous film strip using the SM1 trap antibody and the SM2 labelled antibody that was the same as in Example 1.

A solution (AC solution) was prepared by adding 12.0% by weight of sodium chloride to an aqueous solution containing 5% by weight of polyethylene glycol monooctylphenyl ether (produced by Wako Pure Chemical Industries, Ltd.) as a nonionic surface active agent (component (C)) containing 1.0 mol/L of sodium hydroxide (component (A)). An aqueous solution (B solution) containing 0.5 mol/L of tartaric acid (component (B)) was prepared. A solution (D solution) was prepared by adding 12.0% by weight of sodium chloride to a solution containing 1.0 mol/L of tris(hydroxymethyl)aminomethane (component (D)).

75 µL of the AC solution was added to 250 µL of the saliva, followed by stirring, 75 µL of the B solution was then added thereto, followed by stirring, and 50 µL of the D solution was finally added thereto, followed by stirring. 100 µL out of the saliva thus treated was dropped on the strip on the side of the labelled antibody retention. The solution thus treated had pH of 7.2. The concentration of the component (C) in the solution was 0.83% by weight. After 15 minutes from the dropping, the reaction with the trap antibody was confirmed, and the amount of the complex of the SM2 labelled antibody and Streptococci mutans remaining in the labelled antibody retention was visually observed.

The examination described in the foregoing was carried out for three subjects a to c, and evaluations were carried out in the same manner as in Example 1. The results thus obtained are shown in Table 5 below.

TABLE 5

| Subject | Number of colonies of Streptococci mutans on MSB culture medium (CFU/mL) | Reaction with antibody | Amount of remaining antibody in labelled antibody retention |
|---------|---|---|---|
| a | $1.2 \times 10^4$ | − | ± |
| b | $4.3 \times 10^5$ | + | − |
| c | $8.4 \times 10^5$ | ++ | − |

Example 6

The examination was carried out in the following manner by using an antibody-immobilized porous film strip using the SM1 trap antibody and the SM2 labelled antibody that was the same as in Example 1.

A solution (AD solution) was prepared by adding 12.0% by weight of sodium chloride to a solution containing 1.0 mol/L of tris(hydroxymethyl)aminomethane (component (D)) containing 3.0 mol/L of sodium hydroxide (component (A)). A solution (BD solution) was prepared by adding 1.0 mol/L of tartaric acid and 0.5 mol/L of citric acid (component (B)) to a solution containing 1.0 mol/L of tris (hydroxymethyl) aminomethane (component (D)) A solution (C solution) was prepared by adding 2 mol/L of sodium chloride to an aqueous solution containing 5% by weight of polyethylene glycol monooctylphenyl ether (produced by Wako Pure Chemical Industries, Ltd.) as a nonionic surface active agent (component (C)).

40 µL of the BD solution was added to 250 µL of the saliva, followed by stirring, 40 µL of the A solution was then added thereto, followed by stirring, and 40 µL of the C solution was finally added thereto, followed by stirring. 100 µL out of the saliva thus treated was dropped on the strip on the side of the labelled antibody retention. The solution thus treated had pH of 6.9. The concentration of the component (C) in the solution was 0.54% by weight. After 15 minutes from the dropping, the reaction with the trap antibody was confirmed, and the amount of the complex of the SM2 labelled antibody and Streptococci mutans remaining in the labelled antibody retention was visually observed.

The examination described in the foregoing was carried out for three subjects a to c, and evaluations were carried out in the same manner as in Example 1. The results thus obtained are shown in Table 6 below.

TABLE 6

| Subject | Number of colonies of Streptococci mutans on MSB culture medium (CFU/mL) | Reaction with antibody | Amount of remaining antibody in labelled antibody retention |
|---------|---|---|---|
| a | $1.1 \times 10^4$ | − | − |
| b | $3.9 \times 10^5$ | + | − |
| c | $7.7 \times 10^5$ | ++ | − |

Example 7

The examination was carried out in the following manner by using an antibody-immobilized porous film strip using the SM1 trap antibody and the SM2 labelled antibody that was the same as in Example 1.

A solution (A solution) was prepared by adding 25.0% by weight of sodium chloride to an aqueous solution containing 1.0 mol/L of sodium hydroxide (component (A)). A solution (BC solution) was prepared by adding 5% by weight of polyethylene glycol monooctylphenyl ether (produced by Wako Pure Chemical Industries, Ltd.) as a nonionic surface active agent (component (C)) to an aqueous solution containing 0.5 mol/L of citric acid (component (B)). A buffer solution (D solution) containing 2 mol/L of tris (hydroxymethyl) aminomethane (component (D)) was prepared.

40 µL of the D solution was added to 250 µL of the saliva, followed by stirring, 40 µL of the A solution was then added thereto, followed by stirring, and 70 µL of the BC solution was finally added thereto, followed by stirring. 100 µL out of the saliva thus treated was dropped on the strip on the side of the labelled antibody retention. The solution thus treated had pH of 6.9. The concentration of the component (C) in the solution was 0.88% by weight. After 15 minutes from the dropping, the reaction with the trap antibody was confirmed, and the amount of the complex of the SM2 labelled antibody and Streptococci mutans remaining in the labelled antibody retention was visually observed.

The examination described in the foregoing was carried out for five subjects a to e, and evaluations were carried out in the same manner as in Example 1. The results thus obtained are shown in Table 7 below.

TABLE 7

| Subject | Number of colonies of Streptococci mutans on MSB culture medium (CFU/mL) | Reaction with antibody | Amount of remaining antibody in labelled antibody retention |
|---|---|---|---|
| a | $3.8 \times 10^4$ | − | − |
| b | $1.6 \times 10^5$ | − | − |
| c | $4.7 \times 10^5$ | ± | ± |
| d | $7.2 \times 10^5$ | + | ± |
| e | $9.2 \times 10^5$ | ++ | − |

Comparative Example 1

The same examination as in Example 1 was carried out for five subjects a to e except that the AD solution containing no sodium chloride was used, and evaluations were carried out in the same manner as in Example 1. The results thus obtained are shown in Table 8 below.

TABLE 8

| Subject | Number of colonies of Streptococci mutans on MSB culture medium (CFU/mL) | Reaction with antibody | Amount of remaining antibody in labelled antibody retention |
|---|---|---|---|
| a | $1.2 \times 10^4$ | − | + |
| b | $2.1 \times 10^5$ | − | + |
| c | $4.5 \times 10^5$ | ± | + |
| d | $7.3 \times 10^5$ | + | + |
| e | $9.2 \times 10^5$ | ++ | + |

Comparative Example 2

The same examination as in Example 4 was carried out for three subjects a to c except that the D solution containing no sodium chloride was used, and evaluations were carried out in the same manner as in Example 1. The results thus obtained are shown in Table 9 below.

TABLE 9

| Subject | Number of colonies of Streptococci mutans on MSB culture medium (CFU/mL) | Reaction with antibody | Amount of remaining antibody in labelled antibody retention |
|---|---|---|---|
| a | $1.0 \times 10^4$ | − | + |
| b | $3.9 \times 10^5$ | ± | + |
| c | $7.7 \times 10^5$ | ++ | + |

It was confirmed from the foregoing results that the pretreatment method for saliva by using the pretreatment kit for saliva according to the present invention could remove aggregation caused by mucin and chain formation of streptococci mutans in saliva, and since the amount of the complex of the labelled antibody and the streptococci mutans remaining in the labelled antibody retention was small, the effect of preventing such a phenomenon that the complex of the labelled antibody and the streptococci mutans remained in the membrane retaining the labelled antibody was confirmed.

As having been described in detail, upon identification and quantitative determination of streptococci mutans, which is a type of cariogenic bacteria in human saliva, by immunochromatography utilizing an antigen-antibody reaction, the pretreatment kit for saliva and the pretreatment method for saliva according to the present invention can remove aggregation caused by mucin and chain formation of streptococci mutans in saliva in a simple operation, and can efficiently flow a complex of a labeled antibody and streptococci mutans from a porous membrane retaining the labeled antibody, whereby identification and quantitative determination can be carried out with high accuracy. Therefore, it provides significant value by contributing to the field of dentistry.

What is claimed is:

1. A pretreatment kit for saliva comprising
   (A) an aqueous solution of sodium hydroxide having a concentration of 0.01 to 10 mol/L,
   (B) an aqueous solution of tartaric acid and/or citric acid having a concentration of 0.01 to 3 mol/L, and
   (C) a nonionic surface active agent and/or an amphoteric surface active agent, the component (C) being mixed with at least one of the components (A) and (B), or being provided separately from the components (A) and (B), and
   at least one substance selected from the group consisting of sodium chloride, potassium chloride, calcium chloride, magnesium chloride, magnesium sulfate and manganese sulfate being contained in at least one of the components (A), (B) and (C) in an amount of 5 to 25% by weight, wherein at least one of (A) and (C) is capable of removing aggregation caused by mucin or chain formation of Streptococci mutans in saliva.

2. A pretreatment kit for saliva as claimed in claim 1, further comprising (D) tris(hydroxymethyl)aminomethane which is mixed with at least one of the components (A), (B) and (C).

3. A pretreatment kit for saliva as claimed in claim 1, wherein the nonionic surface active agent as the component (C) is one kind or a mixture of two or more kinds selected from the group consisting of polyethylene glycol monooctylphenyl ether, n-octyl-β-D-glucoside, n-heptyl-β-D-thioglucoside, n-octyl-β-D-thioglucoside, nonylphenoxy polyethoxyethanol and polyoxyethylene sorbitan monooleate.

4. A pretreatment kit for saliva as claimed in claim 1, wherein the amphoteric surface active agent as the component (C) is at least one agent selected from the group consisting of CHAPS (3-(3-cholamide-propyl)-dimethylammonio)-1-propanesulfonate) and CHAPSO (3-(3-cholamide-propyl)-dimethylammonio)-1-hydroxypropanesulfonate).

* * * * *